United States Patent [19]

Nemcek et al.

[11] 4,374,937

[45] Feb. 22, 1983

[54] DISPERSIONS OF SILICEOUS SOLIDS IN LIQUID ORGANIC MEDIA

[75] Inventors: Jozef Nemcek, Chester; Thomas A. Roberts, Congleton; Francis R. Sherliker, Runcorn, all of England

[73] Assignee: Imperial Chemical Industries Limited, London, England

[21] Appl. No.: 279,319

[22] Filed: Jul. 1, 1981

Related U.S. Application Data

[63] Continuation of Ser. No. 106,861, Dec. 26, 1979, abandoned.

[30] Foreign Application Priority Data

Jan. 5, 1979 [GB] United Kingdom ............... 7900363
Jan. 5, 1979 [GB] United Kingdom ............... 7900364
Jan. 5, 1979 [GB] United Kingdom ............... 7900366
Jan. 5, 1979 [GB] United Kingdom ............... 7900367
Apr. 4, 1979 [GB] United Kingdom ............... 7911712

[51] Int. Cl.$^3$ .......................... C08J 3/20; C08K 5/17; C08K 5/52

[52] U.S. Cl. .................................. 523/116; 523/443; 523/506; 523/508; 524/141; 524/140; 524/243; 524/246; 524/710; 524/714; 524/722; 204/159.23

[58] Field of Search ............... 523/116, 443; 524/710, 524/714, 722

[56] References Cited

U.S. PATENT DOCUMENTS 4,221,697  9/1980  Osborn et al. .................. 260/42.53
4,251,576  2/1981  Osborn et al. .................. 260/42.14

FOREIGN PATENT DOCUMENTS 1202046  8/1970  United Kingdom .

*Primary Examiner*—Carman J. Seccuro
*Attorney, Agent, or Firm*—Cushman, Darby & Cushman

[57] ABSTRACT

Dispersions of colloidal siliceous particles, preferably silica, may be prepared in organic liquids by means of a synergistic mixture of dispersing agents comprising a phosphorus oxy-acid derivatives and a long-chain amine. Dispersions containing a high weight fraction of siliceous solids are possible having a lower viscosity than is normally achieved.

27 Claims, No Drawings

DISPERSIONS OF SILICEOUS SOLIDS IN LIQUID ORGANIC MEDIA

This is a continuation of application Ser. No. 106,861, filed Dec. 26, 1979, now abandoned.

This invention relates to compositions in which a solid phase is dispersed in a liquid phase.

When dispersions are made of siliceous solid materials for example finely divided silica in organic liquids the solid particles tend to cohere and the dispersion thickens or gels and even becomes a solidified mass at quite low concentrations of the solid particles. For example untreated silica having a surface area of 200 m² per g will form a sludge with methyl methacrylate at ca 5% which will not pour or flow at a concentration of as little as 8%.

Methods are known for the pre-treatment of the surface of the silica and treated silica particles are available which will allow larger concentrations of silica to be dispersed before gelling of the dispersion occurs.

We have now found that it is not necessary to pre-treat the silica and that the addition of a combination of additives allows superior liquid dispersions to be made containing higher concentrations of solid siliceous materials than have been possible hitherto.

It is desirable for many applications of solid/liquid compositions to have the maximum possible of the solid phase properly dispersed in a two phase composition which nevertheless retains some fluidity.

According to the present invention there is provided a composition comprising the following components (a-c) intimately mixed together:

(a) a particulate siliceous material having particles below 10 μm in their longest dimension;

(b) a liquid or liquifiable organic medium as hereinafter defined;

(c) a dispersing agent containing a mixture of compounds comprising a phosphorus oxyacid having the formula:

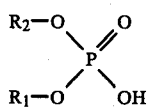

wherein $R_1$ is an organic group containing a terminal chain which is either a hydrocarbon group having at least six carbon atoms or a polyether of molecular weight greater than 200 preferably from 500–10,000, $R_2$ is either a group as specified for $R_1$, a hydrogen atom, or a hydrocarbyl or substituted hydrocarbyl group not having a terminal chain of at least six carbon atoms and an organic basic nitrogen compound having the formula:

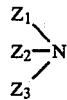

wherein $Z_1$ is a group as specified for $R_1$ above and $Z_2$ and $Z_3$, which may be the same or different, are as specified for $R_2$ above.

The particulate siliceous material may be for example a silicate salt e.g. aluminium silicate or calcium silicate or a silicate-containing mineral in finely divided form e.g. talc, but it is preferably silica itself.

The particulate silica may be any form of silica including comminuted forms of crystalline silicas e.g. sand, but is preferably a colloidal form e.g. a pyrogenic or fumed silica having particles of sub micron dimensions.

The silica normally used is the pure untreated silica powder but surface-treated forms may be used, for example silane-treated silica wherein the surface is rendered more hydrophobic than normal. The particle size of the siliceous material is preferably less than 1 μm for the largest dimension and commonly silicas having a surface area of 50–300 m²/g are eminently suitable for the compositions of this invention.

Each of the compounds of the dispersing agent also contains a chain-like group and it is thus an amphipathic compound preferably containing a chain which is solvated by the liquid or liquifiable organic medium component (b) of the composition. The term solvatable is used in the sense that if the chain-like group were an independent molecule the liquid medium would be significantly better than a "theta solvent" for it. The nature of a "theta solvent" is discussed in "Polymer Handbook" (Ed. Brandrup and Immergut Interscience 1966) and in "Principles of Polymer Chemistry" Chapters 12–14 (Flory: Corwell 1953). Alternatively the liquid medium may be described as being a good solvent for the chain-like group of the compounds in the dispersing agent when one or other or both are chosen to fulfill this preferred condition. When the nature of one is known, for example usually the organic medium because this makes the largest contribution to the utility of the composition, the other may be matched to it by means of this solubility criterion.

Furthermore, the dispersing agent comprises compounds which also contain special chemical groupings, namely the phosphorus oxyacid and the amino groups which surprisingly are capable of co-acting or co-operating together to produce a very pronounced dispersing effect, considerably greater than that observed when either of the groups is used alone.

The organic liquid or liquifiable organic medium should not contain acidic or basic groups (e.g. COO⁻, $NH_2$) and is preferably either a polymerisable liquid for example a liquid monomer containing a vinyl, epoxy or other polymerisable group or a liquid containing functional groups reactive with condensation catalysts or promotors. For example amongst the liquids containing functional groups we prefer those containing hydroxyl groups especially diols and polyols for example those conventionally used to react with isocyanates to make polyurethanes or vinyl urethanes, such as for example those described in British Pat. Nos. 1,352,063, 1,465,097, 1,498,421 and German Offenlegungschrift No. 2,419,887 or the reaction product of a diol particularly a bisphenol with a glycidyl alkacrylate such as those described for example in U.S. Pat. Nos. 3,066,112 and 4,131,729 (the disclosures in these specifications are incorporated herein by way of reference).

A preferred reaction product of a glycidyl alkacrylate and a diol has the formula

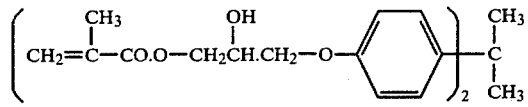

Preferred vinyl urethanes described in the aforesaid British Patent Specifications and German Offenlegungschrift are the reaction product of a urethane prepolymer and an ester of acrylic or methacrylic acid with a hydroxy alkanol of at least 2 carbon atoms, the urethane prepolymer being the reaction product of a di-isocyanate of the structure OCN—$R^1$—NCO and a diol of the structure HO—$R^2$—OH wherein $R^1$ is a divalent hydrocarbyl group and $R^2$ is the residue of a condensate of an alkylene oxide with an organic compound containing two phenolic or alcoholic groups.

Amongst the polymerisable liquids we prefer to use readily available common monomers from the classes including hydrocarbons, ethers, esters and amides for example, styrene, vinyl ethyl ether, vinyl acetate, methyl methacrylate, ethyl acrylate, butyl methacrylate, ethyl cyanoacrylate, divinyl benzene, glycol dimethacrylate, styrene oxide, tetrahydrofuran, caprolactam and caprolactone.

It is desirable for the liquid medium to be a stable inert liquid at ambient temperatures because the requisite dispersion of siliceous particles is more easily effected if no heating is required for the liquefaction of the said medium. However, compounds which are solid or semi-solid at ambient temperatures may be used, the compositions normally being prepared at an elevated temperature above the melting point or softening point of the medium, this temperature should suitably be below 250° C. and preferably below 150° C.

The phosphorus oxyacid compound containing the groups $R_1$ and $R_2$ is preferably a compound readily prepared by simple chemistry and ideally one available commercially. Therefore the group $R_1$ is preferably either a hydrocarbyl group, especially a long-chain alkyl group containing from 8 to 22 carbon atoms or a polyether or polyester chain. For ready availability we conveniently select from hydrocarbons the common alkyl groups including octyl, decyl, dodecyl, hexadecyl and octadecyl groups in normal or branched form or alkyl benzene groups, also polyoxyethylene, polyoxypropylene or polytetramethylene oxide chains and copolymers thereof from amongst the polyether groups possible and polycaprolactone from amongst the polyester chains.

The group $R_2$ is preferably hydrogen, methyl, ethyl, phenyl, benzyl or a group identical to $R_1$.

Compounds especially preferred include:
di(2-ethylhexyl)phosphoric acid
n-hexadecyl phosphoric acid
mono(methoxy polypropylene oxy)phosphoric acid
di(methoxy polypropylene oxy) phosphoric acid The basic nitrogen compound is preferably one containing a group $Z_1$ which is an alkyl group especially $C_8$-$C_{22}$ alkyl, or a polyethylene oxy or polypropylene oxy group. The groups $Z_2$ and/or $Z_3$ in preferred compounds are either similar to the preferred group for $Z_1$ or are hydrogen, lower alkyl (especially methyl and ethyl) phenyl or benzyl. Examples of especially preferred amines are long chain amines such as those available commercially under the trade names of "Ethomeen" "Armeen" and "Synprolam" e.g. "Synprolam" 35 and "Synprolam" 35×15. "Ethomeen" "Armeen" and "Synprolam" are Registered Trade Marks.

The weight concentration of the dispersing agent to be used in the composition of this invention is not critical but if a measure is taken it needs to be related mainly to the weight of the siliceous particles present in the composition. We have found that noticeable results are obtainable from 0.1% by weight but in general there is no further improvement beyond 40% by weight of dispersing agent relative to weight of siliceous particles. For best results we prefer to use from 1% to 10% by weight of the dispersing agent.

The molar proportion of acids to bases in the dispersing agent may be from 0.5:1 to 100:1 but it is better to have an approximately 50% molar excess of acid present and therefore preferred proportions are from 1:1 to 3:1 measured as molar ratios of acid to base.

The main purpose of the compositions herein disclosed is to provide a solid liquid dispersion containing a high solids content. The dispersing agent allows this by reducing considerably the tendency of siliceous solid materials to gel or otherwise cohere together and set to a solid mass which cannot be further fluidised. This tendency is minimised and large quantities, for example up to 30–40% by weight and sometimes more e.g. up to 90% by weight, of the solid may be dispersed in the liquid. The resulting composition is still mobile whereas a solid mass would result without the presence of the dispersing agent or even without one component (the acid or the base) of the dispersing agent. Therefore in order to realise the advantage of the invention the compositions will suitably contain more than 5% and preferably 20–50% by weight of the solid material in the total composition.

The major application of the compositions of this invention lies in the use of liquids which will polymerise or otherwise react to form polymers. Moulded or cast articles for example, sheet, films, rods, tubes and including articles especially moulded or cast into a variety of shapes having a specific utility for example handles, knobs, wheels, lids, sanitary ware, etc. or rubbery products e.g. tyres, shoe-soles, gloves may conveniently and advantageously be made from these compositions; the dispersed solid provides a useful reinforcing, hardening or decorative effect to the finished article which often shows an increased resistance to solvent attack also.

In general the higher the concentration of solid materials which may be uniformly dispersed in the liquid the stronger will be the final moulded article. Therefore there is considerable advantage to be gained from the use in the composition of the dispersing agent since it allows uniform, tractable dispersions of the solid to be made and used conveniently for the production of strong articles having a high modulus and containing high proportions (often over 40% by weight) of a siliceous solid still well dispersed even in the solidified article. The best known form of silica for increasing the strength of moulded polymers is colloidal silica, and we prefer to use the invention in order to produce shaped articles (e.g. by moulding or casting) of organic polymers, especially polymethyl methacrylate containing high concentrations of silica as a reinforcing filler. Normally a fine colloidal silica dispersed in an organic monomer sets to a solid mass at a solids concentration of ca 7% but in a composition according to the present invention 35% of silica may be present and yet the composition is readily handled because it is still a pourable liquid composition.

Advantageously a reactive silane for example dimethyl dichlorosilane or an ethoxy silane but especially a silane containing polymerisable groups, conveniently α-methacryl oxypropyl trimethoxy silane may be incorporated in the compositions of the invention. By this means dispersions containing a still higher proportion of silica may be prepared leading to superior mechanical properties of the polymerised composition, especially toughness.

Where the liquid medium is a vinyl urethane, optionally mixed with 50% to 150% by weight of the vinyl urethane of at least one ethylenically unsaturated copolymerisable monomer, the present compositions are useful as dental compositions particularly in the preparation of denture base, orthodontic adhesives and artificial teeth. The dental compositions may include free-radical generating catalyst systems such as for example those based on an organic peroxide or light-cure catalyst system for example that described in British Pat. No. 1,408,265 (the disclosure of which is incorporated herein by way of reference).

According to a particular aspect of the present invention there is provided a dental composition which is a fluid composition comprising (a) a particulate siliceous material having particles below 10 μm in their longest dimension, (b) a polymerisable prepolymer containing at least two polymerisable ethylenically unsaturated groups and being the reaction product of a urethane prepolymer and an ethylenically unsaturated monomer reactive with the urethane prepolymer, (c) a dispersing agent containing a mixture of compounds comprising a phosphorus oxyacid having the formula:

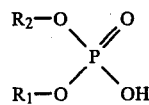

where $R_1$ is an organic group containing a terminal chain which is either a hydrocarbon group having at least six carbon atoms or a polyether of molecular weight greater than 200 preferably from 500–10,000, $R_2$ is either a group as specified for $R_1$, a hydrogen atom, or a hydrocarbyl or substituted hydrocarbyl group not having a terminal chain of at least six carbon atoms and an organic basic nitrogen compound having the formula:

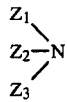

wherein $Z_1$ is a group as specified for $R_1$ before and $Z_2$ and $Z_3$ which may be the same or different are as specified for $R_2$ before, (d) at least one photosensitiser selected from fluorenone, substituted derivatives thereof, and α-diketones having the structure

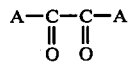

in which the groups A, which may be the same or different, are hydrocarbyl groups or substituted hydrocarbyl groups and (e) at least one reducing agent capable of reducing the photosensitiser when the photosensitiser is in an excited state.

By fluid composition we mean a composition which has sufficient mobility that it may be readily moulded at ambient temperature, for example, merely by moulding under hand pressure. Suitably, the composition will have a paste-like consistency.

The dental composition may be applied to the tooth, e.g. as a filling to a cavity in the tooth, and the polymerisable prepolymer may be polymerised so that the composition is formed into a hard material. This polymerisation process will hereinafter be referred to as curing of the composition.

The composition may contain a polymerisable prepolymer which is a solid or semi-solid and as the siliceous material is also solid it is often necessary (in order to produce a composition which is fluid) to add to the composition sufficient liquid ethylenically unsaturated monomer copolymerisable with the polymerisable prepolymer to make the composition fluid, and in particular to give the composition a paste-like consistency. If desired, the composition may include liquid copolymerisable ehtylenically unsaturated monomer even where the polymerisable prepolymer is itself a liquid.

The dental compositions of the present invention may be cured by irradiating the composition with ultraviolet radiation, that is, with radiation having a wavelength in the range about 230 mμ up to 400 mμ. The compositions may also be, and preferably are, cured by irradiating with visible radiation and especially with visible radiation having a wavelength in the range 400 mμ to 500 mμ. Alternatively, a mixture of ultraviolet and visible radiation may be used.

Suitably the concentration of the photosensitiser is 0.001% to 10% by weight, preferably 0.1% to 5% by weight and the concentration of reducing agent is 0.25% to 5% by weight preferably 0.25% to 0.75% by weight, all these percentages being by weight of the polymerisable material in the dental composition.

The polymerisable material in the dental composition is a polymerisable ethylenically unsaturated material. Preferably at least part of the material containing a plurality of ethylenically unsaturated groups is such that polymerisation of the material results in the production of a cross-linked polymer.

In order that the cured dental composition should possess higher strength and modulus it is preferred that the polymerisable material possesses at least one cyclic group. In the case where the polymerisable material includes a plurality of ethylenically unsaturated groups it is preferred that the material possesses at least one cyclic group in the chain between the ethylenically unsaturated groups.

Mixing of the polymerisable prepolymer with the siliceous filler to form the dental filling composition may be effected by stirring together the prepolymer and the filler. However, as the polymerisable prepolymer, optionally together with a copolymerisable monomer, may be viscous and thus difficult to stir with the filler so as to achieve adequate mixing the polymerisable prepolymer, optionally together with copolymerisable monomer, may conveniently be diluted with a suitable diluent so as to reduce the viscosity thus enabling adequate mixing of the filler to be more readily achieved. When mixing has been effected the diluent may be removed, e.g. by evaporation. Suitably, the diluent may be copolymerisable ethylenically unsaturated monomer, the level of the monomer subsequently being reduced to the desired extent.

In order that a dental filling composition may be produced in which the siliceous filler in the composition adheres particularly well to the cured polymerisable prepolymer it is much preferred that the filler be treated with a coupling agent which is capable of reacting with both the siliceous particles and the polymerisable prepolymer before the mixing of the filler and polymerisable prepolymer is effected. The coupling agent should have the effect of increasing the strength of the bond between the filler and the cured polymerisable prepolymer in the filling.

Suitable coupling agents especially for use with glass or silica include silanes, e.g. γ-methacryloxypropyltrimethoxysilane, γ-aminopropyltriethoxysilane and γ-glycidoxypropyltrimethoxysilane.

As stated hereinbefore, the dental composition may contain liquid ethylenically unsaturated monomer copolymerisable with the polymerisable prepolymer, and should contain such a monomer when the polymerisable prepolymer is a solid in order that the dental filling composition be fluid and in particular have a paste-like consistency.

The amount of such ethylenically unsaturated monomer used may desirably be just sufficient to achieve the desired fluidity in the dental filling composition. As the use of such a monomer may lead to a reduction in the strength of the dental filling made from the composition it is preferred to use in the filling composition not more than 100% of ethylenically unsaturated monomer by weight of polymerisable prepolymer, and more preferably not more than 50% by weight.

Suitable liquid copolymerisable ethylenically unsaturated monomers, the polymers of which should be water insoluble, include vinyl monomers, e.g. vinyl esters and acrylic and methacrylic acids. The monomers should be non-toxic.

Polyfunctional vinyl monomers, that is, monomers containing two or more vinyl groups are also suitable. Suitable monomers include, for example, glycol dimethacrylate, diallyl phthalate, and triallyl cyanurate.

In order that the dental base and/or artificial teeth may have flesh coloured and/or natural appearance, the present composition may include small quantities of pigments, opalescent agents and the like.

The composition of the present invention may be used for a range of dental applications having regard to the consistency of the composition. They may be used as filling materials (posterior and anterior), dental glazes (particularly for posterior teeth) and orthodontic adhesives. In particular the composition should have a stiff paste or doughy consistency if it is to be used as a filling material; it should be a liquid preferably flowable if it is to be used as a dental glaze so that it may be applied to the prepared tooth surface e.g. by brushing and thereafter flow before curing so as to product a smooth surface. If the composition is to be used as an orthodontic adhesive, then a wide range of consistency is envisaged depending on what is to be adhered to the tooth and the way in which the adhesive is to be applied; for example where a dental bracket is to be adhered to a tooth the composition may be a liquid so that it may be applied to the tooth and the bracket pressed into the liquid film or the composition may be a dough which is applied to the back of the bracket or to a small area of the tooth surface before mating the tooth and bracket. Accordingly the present composition is coherent and not crumbly or powdery.

The dental composition of the present invention may conveniently be packed in small containers (e.g. 1 g capacity) so as to facilitate handling in the surgery and reduce the risk of inadvertent curing by stray light.

It is preferred that the surface of the tooth be cleaned before application of the composition. The tooth may be so cleaned by for example grinding with a rotating wheel or brush or by etching using for example aqueous phosphoric acid.

It is desirable for the liquid medium to be a stable inert liquid at ambient temperatures because the requisite dispersion of siliceous particles is more easily effected if no heating is required for the liquefaction of the said medium. However, compounds which are solid or semi-solid at ambient temperatures may be used, the compositions normally being prepared at elevated temperature above the melting point or softening point of the medium, this temperature should suitably be below 250° C. and preferably below 150° C.

The invention is illustrated by the following Examples, in which the parts and percentages are by weight.

EXAMPLE 1

The general procedure adopted for making dispersions of silica was to add solvent or monomer to the dispersing agents in a beaker of convenient size e.g. 250 ml. The dispersants were not necessarily dissolved at this stage. Aliquots of dry silica were stirred in by hand using a spatula until a gel was formed. The mix was then stirred at high shear rate using a Greaves compressed air stirrer until the dispersion was fluid and the viscosity was at its minimum. Whenever a predetermined concentration of silica in the dispersion was required further silica was added and the procedure repeated until the total required weight of silica was all dispersed. Whenever a dispersion containing the maximim silica concentration possible was required aliquots of silica were added until the stirring at high shear did not break the gel. At this stage a fluid dispersion could be obtained if a further quantity of the dispersing agents were added and stirring continued without further addition of silica.

Owing to the evaporation of some solvents from the open beaker during the high-shear stirring of the mixture, the final adjustment of the amount of solvent required was made at the end. This was calculated from a knowledge of the individual weights of all the materials added and a measurement of the total weight at the end of the dispersion procedure. Following this procedure a fluid dispersion of 15% wt. pyrogenic silica "Aerosil A130" in methyl methacrylate (MMA) was prepared using the following weights of materials mixed in a 250 ml beaker.

| | |
|---|---|
| Aerosil A130 | 18g |
| Methyl methacrylate | 120g |
| Di(2-ethyl hexyl)phosphoric acid (DEHPA) | 0.54g |
| Armeen 12D | 0.25g |

(long chain alkyl amine produced by Armour Hess = AKZO)

For comparison the silica and methylmethacrylate were stirred at high shear in the same apparatus but without the dispersing agents. When only 6% silica had been added the mixture became non-pourable and only a small further addition of ca 2% produced a gel-like mixture.

EXAMPLE 2

Following the procedure in Example 1, similar 15% by weight dispersion of Aerosil A130 silica were prepared in 120 g of methylmethacrylate. Various total quantities and relative proportions of compounds in the dispersing agent were used as shown in Table I. After the 15% of silica had been added to make a fluid dispersion the mixture was allowed to stand and at selected intervals of time examined for fluidity. The number of days before the dispersion gelled is recorded in the third column of the Table. This gel could be broken down into a fluid dispersion by stirring again at high shear rate.

To a portion of each dispersion silica was added in small quantities with continued stirring until either a permanent gel or a thick paste was obtained. The silica concentration present when this state was reached is recorded in the fourth column of the Table as the maximum concentration of silica dispersed.

For comparison on the same weights of methyl methacrylate and α-methacryl oxypropyl triethoxy silane were used but then two compounds of the dispersing agent were omitted. Silica was added as described in Example 1 and the mixture became non-pourable when 15% silica had been added.

EXAMPLE 5

A fluid dispersion containing 23% weight silica in 120 g methylmethacrylate was prepared using 3% by weight relative to silica of cetyl di-hydrogen phosphetic and 1.8% by weight Armeen 18D.

EXAMPLE 6

A mixture of mono- and di-propoxylated phosphoric acid (approx. 1:1 molar) was made by reacting monomethoxy ended polypropylene glycol (MW 1250) with $P_2O_5$ (3:1 molar ratio) in methylene chloride followed by evaporation of the solvent. This propoxylated phosphate (2.0 g) was used in combination with Armeen 18D 0.8 g. A dispersion containing 34% Aerosil A130 (41 g) in 120 g methylmethacrylate monomer was obtained.

TABLE I

| Effect of Molar Ratio of Additives on the Gel Time of 15% Dispersions of A130 in MMA | | | | |
| --- | --- | --- | --- | --- |
| *Concentration of Dispersing Additives | | Molar Ratio Acid/Amine | Gel Time of 15% Dispersion | Maximum A130 Dispersed in MMA |
| 5% DEHPA | 1% Armeen 18D | 4.0 | 8 days | |
| 3% DEHPA | 1% Armeen 18D | 2.5 | 13 days | 30% |
| 2.4% DEHPA | 1.1% Armeen 18D | 1.8 | 65 days | |
| 3% DEHPA | 1.8% Armeen 18D | 1.4 | 180 days | 38% |
| 4.2% DEHPA | 3.4% Armeen 18D | 1.0 | | 33% |
| 4.7% DEHPA | 4.8% Armeen 18D | 0.8 | | 14% |
| 3.6% DEHPA | 4.8% Armeen 18D | 0.5 | | 12% |

*% age additives based on weight of silica present in a 15% by weight dispersion
DEHPA is Di(2-ethyl hexyl)phosphoric acid

EXAMPLE 3

Employing the procedure described in Example 1 a dispersion of 35% by weight of silica (Aerosil A130) in 120 g methyl methacrylate monomer was prepared using a mixture of 1.25 g di-(2 ethylhexyl) phosphoric acid and 0.75 g Armeen 18D (long chain alkyl amine from AKZO) as the dispersing agent. The dispersion obtained was stable and remained a pourable liquid for a period of about an hour.

After this it gelled but the fluid dispersion could be regenerated by further stirring at high shear. 38% by weight of silica could be added before an immediate gel-point was reached.

For comparison a lower concentration of silica ca. 10% was added by the same procedure using the same total weight (2.0 g) of each of the dispersing agents separately. The composition in each case was a thick paste and no pourable liquids could be made without using the two compounds together in the dispersing agent even at this lower concentration of silica.

EXAMPLE 4

A dispersion containing 42% by weight silica (Aerosil A130) in 120 g methylmethacrylate monomer was prepared using the same amount of the two compounds in the dispersing agent as in Example 3 but adding additionally 6% by weight on silica of α-methacryloxypropyl triethoxysilane. A pourable fluid dispersion was obtained. 48% by weight silica could be added before the gel-point was reached.

EXAMPLE 7

A mixture of mono and di-propoxylated phosphoric acid similar to that of Example 6 was prepared, except that the average molecular weight of the monomethoxy polypropylene glycol was 1800. A dispersion in methylmethacrylate similar to that of Example 6 was prepared with the help of 3.2 g of phosphate (0.5 g) Armeen 18D and 38% Aerosil A130 could be added before the mixture solidified.

EXAMPLE 8

A mixture of mono and di-dodecyl phosphates (approx 1:1 molar ratio) was prepared as in Example 6 and (1.35 g) of this material in combination with 0.52 g Armeen 18D was used in the procedure of Example 1 to obtain fluid dispersion in MMA containing 19% Aerosil A130.

EXAMPLE 9

24 g of Aerosil A130 colloidal silica was taken and relative to this 1.5% "Propomeen" HT25 (propoxylated amine-Armour Hess product) and 3% DEHPA were used in recipe similar to Example 1. Fluid dispersion containing 20% Aerosil A130 in methyl methacrylate was obtained.

EXAMPLE 10

35 g of Aerosil A130 selected for the required weight of silica. Example 1 was repeated, except that 10.6% propoxylated triethanolamine (approx. MW 875) and DEHPA 5.2% were used as dispersing additives. About 29% Aerosil A130 was dispersed in methylmethacrylate at which point the mixture became non-pourable.

EXAMPLE 11

0.56 g Di-methyl-coconut oil amine (mainly C12 chain approx MW 250) and 1.0 g DEHPA were used in this Example. The fluid dispersion at Aerosil A130 in MMA gelled when 39% silica (47 g) was added to 120 g of the methyl methacrylate monomer.

EXAMPLE 12

Amine containing polyester chain was prepared by heating a mixture of 71.3 g of ε-caprolactone, 10 ml of 3-dimethyl aminopropylamine and catalytic amount of tetrabutyltitanate at 160° C.–165° C. for 1 hour. The approximate mol. weight of the product was 1015. 49 g of Aerosil silica was weighed out and based upon this weight 9.7% of above polyester-amine and 4.7% DEHPA was employed using the procedure of Example 1. Dispersions of up to 32% Aerosil MMA could be obtained before the gel point was reached.

EXAMPLE 13

Dispersions of silica were made in a variety of solvents and/or monomers and the maximum concentration of silica was determined by the following procedure.

125 g of the organic liquid was placed in a beaker and to this was added 0.68 g di(2-ethylhexyl)phosphoric acid (DEHPA) and a weight of an amine which would result in a molar ratio of acid to amine of 1.4:1. Silica was added with stirring by hand until a thick gel was formed and then the gel was vigorously stirred at high shear using a Greaves compressed air stirrer. The mixture became fluid once more and more silica could be added. When a gel was observed again a further known quantity of dispersing agent in the same molar ratio of 1.4:1 was added to bring the mixture back to the fluid form again and then more silica added with repeated stirring at high shear. The process of adding aliquots of silica and small quantitites of dispersing agents was continued until no further change was observed, the mixture remaining as a thick grease which could not be made more fluid by increasing the concentration of dispersing agents. From the known weights of all materials added the composition of this final mixture was determined for each organic liquid and the results are shown as percentages by weight in Table II.

TABLE II

| Solvent | Dispersing Agent % Concentration /weight silica | Maximum Silica % Concentration/ weight solvent |
|---|---|---|
| Methylene Chloride | None | 4.5 |
| | DEHPA 4.5% Propaneen HT25 12.5 | 12.5 |
| Carbon Tetrachloride | None | 3.5 |
| | DEHPA 8.5 Armeen 18D 5.0 | 27 |
| Methanol | None | 33 |
| | DEHPA 3.2 Ethomeen T25 5.0 | 49 |
| Acetone | None | 18 |
| | DEHPA 3.0 Armeen 18D 1.8 | 31 |
| Ethyl Acetate | None | 13 |
| | DEHPA 3.0 Armeen 18D 1.8 | 26 |
| Heptane | None | 10 |
| | DEHPA 7.7 Armeen 18D 4.5 | 44 |
| Styrene | None | 8 |
| | DEHPA 8.1 Armeen 18D 4.8 | 16.7 |

EXAMPLE 14

A quantity of silica equal to 30 g was weighed out and Example 1 was repeated using weights of dispersing compounds based on the weight of silica chosen. 3.5% DEHPA and 1.5% Armeen 18D in ethyl acrylate produced a fluid dispersion containing 26% Aerosil A130.

EXAMPLE 15

Following the procedure of Example 1, except that the beaker was heated to 90°–100° C., a fluid dispersion containing 21% A130 in 120 g molten ε-caprolactam was obtained with the help of 4% DEHPA and 1.6% Armeen 12D based on the weight of silica added (25 g)

EXAMPLE 16

A procedure similar to Example 1 was used to disperse precipitated silica 'Ultrasil VN3' in 120 g of a polyol. The polyol used was polypropylene glycol MW 2000 (B56, ex Lankro) containing 20% equivalent triol (T56, MW 3000) Various dispersing systems were used and the results are summarised in Table II.

TABLE II

| Dispersing System | Max silica loading (wt %) for pourable dispersion |
|---|---|
| None | 15 |
| Armeen 18D 0.52g + DEHPA 1.3g | 26.5 |
| DMEPO 1.1g + DEHPA 1.3g | 25 |
| Armeen 18D 0.52g + PPOP 3.1g | 40 |

DMEPO = propoxylated dimethylethanolamine (MW = 1000)
PPOP = mono and di propoxylated phosphoric acid
DEHPA = Di(2-ethylhexyl)phosphoric acid

EXAMPLE 17

Following the procedure of Example 16 but replacing Ultrasil with Aerosil R972 (pyrogenic silica coated with dimethyl dichlorosilane to make it hydrophobic) and employing 1.3 g DEHPA and 0.52 g Armeen 18D as dispersants a pourable dispersion containing 30% silica was prepared.

EXAMPLE 18

The dispersing agents Armeen 18D (a long chain amine) and Di(2-ethylhexyl) phosphoric acid were used at concentrations of 1.0% and 2.5% respectively based on the weight of silica to make polyurethane compositions filled with pyrogenic silica. Three polyurethane elastomer compositions were made from a polyol and a slight molar excess of di-phenyl methane diisocyanate (MDI). Whilst the reactants were in the liquid form the silica and dispersing agents were mixed with high shear stirring until a uniform mix was obtained and then the mixture was poured into a mould and reacted in the mould to form a solid polymer. Conveniently some polymer samples were moulded into blocks on which physical properties could be evaluated and the physical properties obtained for various silica-filled blocks are shown in Table III compared with unfilled blocks of the same polyurethane.

TABLE III

| wt % silica | Tensile Strength $MNm^{-2}$ | Tear Strength $KNm^{-1}$ | % Elongation to break | Hardness Shore A |
|---|---|---|---|---|
| 0 | 1.2 | 4.0 | 650 | 39 |
| 16.4 | 8.0 | 36.9 | 1000 | 62 |
| 25.4 | 19.7 | 67.5 | 1000 | 69 |
| 14.0 | 8.5 | 32.5 | 1000 | 52 |

TABLE III-continued

| wt % silica | Tensile Strength MNm$^{-2}$ | Tear Strength KNm$^{-1}$ | % Elongation to break | Hardness Shore A |
|---|---|---|---|---|
| 14.7 | 7.8 | 33.5 | 1000 | 52 |
| 0 | 4.9 | 22.1 | 800 | 70 |
| 17.6 | 20.2 | 49.4 | 950 | 75 |
| 18.1 | 17.9 | 63.2 | 1000 | 75 |
| 0 | 0.8 | 4.5 | 680 | 37 |
| 15.3 | 10.6 | 47.2 | 1000 | 60 |
| 23.8 | 16.5 | 66.6 | 1000 | 65 |

EXAMPLE 19

Dispersions of silica in methyl methacrylate monomer (containing 0.04% AD1B catalyst) were made at various concentrations using the method described in Example 1, and the dispersions were poured into casting cells constructed of sheets of plate glass separated by a 3 mm PVC gasket. The casting cells were sealed and degassed by immersing the complete cell into an ultrasonic bath for about 30 minutes. The cells were then immersed in a water bath at 55° C. and left for ca. 16 hours to polymerise the monomer. The bath temperature was then raised to 65° C. for one hour and to 70° C. for three hours. The cell was then dismantled and the solid sheet of silica-filled polymer was removed and placed in an oven at 110° C. to complete the polymerisation.

Samples were cut from the sheet and various physical properties were measured. The results are shown in Table IV.

TABLE IV

| Type of Silica | % silica by weight | Flex. Strength MNm$^{-2}$ | Flex. Modulus GNm$^{-2}$ | Impact Strength Kg cm$^{-2}$ | Barcol* Hardness |
|---|---|---|---|---|---|
| Aerosil A 130 | 19 | 62 | 3.8 | | 67 |
| Aerosil A 130 | 23 | 64 | 4.4 | 2.5 | 69 |
| Aerosil A 130 | 18 | 131 | 3.7 | 7.3 | 67 |
| cont/g | 23 | 148 | 4.0 | 4.2 | 70 |
| 6% silane | 30 | 122 | 4.5 | 5.9 | 71 |
| — | 0 | 136 | 2.7 | 10.3 | 55 |

*on the same method of measurement glass gave a value of 80

EXAMPLE 20

35.2 g (0.1 mole) of the condensate obtained by reacting 2,2-bis-(4-hydroxyphenyl)propane and propylene oxide in a molar ratio of 1:2 (oxypropylated Bisphenol A) were dissolved in approximately 100 g of methylene dichloride and the resulting solution was added dropwise to a solution of 33.6 g (0.2 mole) of hexamethylene di-isocyanate in 100 g of methylene dichloride under an atmosphere of nitrogen gas. 4 drops of dibutyl tin dilaurate (available as "Mellite" 12, "Mellite" is a registered Trade Mark) were added as catalyst. The mixture was stirred under nitrogen for 1 hour after which it was heated under reflux conditions for 9 hours. The mixture was then cooled and a solution of 29 g (0.2 mole) of hydroxypropyl methacrylate in 100 g of methylene dichloride was added after which the mixture was heated under reflux conditions for 3 hours. The hydroxypropyl ester comprised isomers in weight ratio 2-hydroxypropyl (2.6 parts) to 1-methyl-2-hydroxyethyl (1 part). The mixture was then cooled and the resulting polymerisable vinyl urethane prepolymer was isolated as a viscous gum by treatment of the mixture with petroleum ether followed by removal of residual solvent in a rotary evaporator.

The vinyl urethane prepolymer (50 g sample) was mixed with triethylene glycol dimethyacrylate (50 g) to produce a liquid organic medium (b).

Liquid organic medium (100 g), dimethyl long-chain alkyl tertiary amine (0.6 g Armour Hess "Armeen" DM 16D), di-(2-ethylhexyl) phosphoric acid (1.00 g) and methacryl silane (1.33 g Union Carbide Corporation grade A 174) were premixed by stirring. Silica (25% by weight based on premix Aerosil A 130) was added progressively whilst the mixture was stirred and further mixed by milling on a twin roll mill followed by repeated evacuation to remove air. The resulting dispersion was clear and had a grease-like texture.

To the dispersion were added benzoyl peroxide (0.5% w/w) and N-N-dimethyl-p-toluidine (0.5% w/w) with stirring. This mixture cured rapidly at room temperature to produce a hard and intractable material and when cured in a mould produced an excellent denture base.

EXAMPLE 21

A mixture was prepared with the following ingredients

| | |
|---|---|
| β-Cristobalite sand (average particle size ca 5 μm) | 2425 g |
| Methyl methacrylate monomer | 1031 g |
| Di(2-ethyl hexyl)phosphoric acid | 15.3 g |
| Armeen 18D long chain amine | 10.7 g |
| Silane A174 | 6.7 g |
| De-mineralised water | 1.4 g |

The ingredients were charged into a 2-gallon porcelain laboratory ball-mill and ground for 24 hours. A low viscosity dispersion resulted which could be poured out in a series of moulds for making plaques by polymerisation of the monomer/silica mixture. Before polymerisation 2% by weight Perkadox 16 and 1% by weight ethylene glycol dimethacrylate were added to the mixture, the percentages being based on the weight of the methyl methacrylate monomer in the mixture. Each mould was immersed in a water bath at 65° C. for 30 minutes and another bath at 80° C. for 30 minutes in order to thermally polymerise the mixture.

Plaques of silica-filled polymer were removed from the moulds and tested for mechanical properties with the following results compared with standard silica-filled polymethyl methylmethacrylates in parenthisis

| | | |
|---|---|---|
| Modulus | 12.5 GN/m$^2$ | (10–12) |
| Flexural strength | 110–120 MN/m$^2$ | (107) |
| Impart | 4–6 KJ/m$^2$ | (4.3) |

EXAMPLE 22

Weights of the two compounds in the dispersing agents as shown in Table V were added to 188 g methyl methacrylate monomer in a beaker of convenient size (e.g. 500 ml). Aliquots of dry pyrogenic silica, "Finsil" 600, were added by hand using a spatula until the weights and corresponding weight fractions shown in Table V were obtained. Each mixture was stirred at high speed using an ILA homogeniser in order to ensure uniform dispersion of the silica. The viscosity of each mixture was measured on a Brookfield RVT viscometer at 21° C. and 100 rpm and the results obtained for each mixture are shown in Table V.

TABLE V

| Weights of components in g | | | Weight fraction of silica | Viscosity in poises |
|---|---|---|---|---|
| Finsil 600 | DEHPA | Armeen C | | |
| 49.2 | 0.98 | 0.44 | 20 | 0.15 |
| 111.4 | 2.20 | 0.99 | 37 | 14.2 |
| 191.1 | 3.79 | 1.70 | 50 | 54.0 |
| 300.7 | 5.89 | 2.64 | 60 | 176.0 |

At high weight fractions of silica the mixture is a very viscous liquid but the presence of the dispersing agent enables some flow to be maintained. Without the dispersing agent the silica and methyl methacrylate mixture is very much more viscous even at low weight fractions of silica. For comparison, when the Finsil 600 MMA monomer were stirred at high shear in the ILA homogeniser without any dispersing agent, the viscosity was measured as 0.59 poises for a 20% weight fraction of silica and the mixture became a dry paste which would not flow at 37% weight fraction of silica.

EXAMPLE 23

To one sample of the dispersion (described in Example 20) were added camphorquinone (0.75% w/w) and dimethylaminoethyl methacrylate (0.5% w/w), and the resulting mixture was milled on a twin-roll mill. To another sample of the dispersion (described in Example 20) were added camphorquinone (0.75% w/w) and long chain alkyl dimethyl tertiary amine (0.5% w/w "Armeen" DM 14D Armour Hess) and the resulting mixture was also ball-milled.

Samples of the two mixtures which were fluid paste compositions were cured on a rheometer described in British Standard 5199: 1975 (specification for resin-based dental filling materials), paragraph 6.4. The setting was effected by exposing the sample under test to the end of Quartz optic light guide length 11 cm. diameter 8 mm. coated along its length with a Netlon sleeve (trade mark) and shrink wrap coating of polyvinyl chloride. The light source was a tungsten halogen lamp 12 volt, 75 watt (Thorn Electrical Al/230). Both samples had cured fully after 30 seconds exposure.

EXAMPLE 24

Two compositions according to the present invention were evaluated as orthodontic adhesives. One composition (A) had the formulation described below and the other composition (B) had the formulation described in Example 23.

| Composition A: | g. |
|---|---|
| Vinyl urethane (described in Example 20) | 134 |
| Triethyleneglycoldimethacrylate | 134 |
| Silica (A 130) | 89.3 |
| Silane (A 174) | 6.25 |
| Di-(2-ethylhexyl)phosphoric acid | 3.57 |
| Tertiary amine ("Armeen" DM16D) | 3.13 |
| Dimethylaminoethylmethacrylate | 2.01 |
| Camphorquinone | 2.68 |

The components were mixed as described in Example 20. In order to determine bond strength of a dental bracket to a tooth, a human tooth was first placed in a clamp and the buccal surface etched with 37% aqueous phosphoric acid for 1 minute. The acid was then washed off with distilled water and the tooth surface dried with compressed air. The orthodontic bracket base was then painted with the adhesive composition and placed on the prepared tooth surface. The adhesive was then cured by transillumination or by direct illumination using a range of cure times using the lamp and guide described in Example 23. After 10 minutes a ligature wire was attached to the bracket and weights were suspended from the ligature wire. The maximum weight which could be supported by the bracket before adhesive failure was recorded. The following types of orthodontic brackets were used:

1. Mesh backed, single edgewise brackets which allow cure of the adhesive composition by radiation through the bracket (e.g. perforated brackets in table below)
2. Foil covered brackets which rely on transillumination through the tooth for cure of the adhesive composition (e.g. Forestadent brackets in table below).

TABLE VI

| Composition | Bracket | Cure method | Supported Load Kg. | Lamp Intensity at 470 nm (Watts/m$^2$) |
|---|---|---|---|---|
| A | Perforated CM1-209 | 1 min. direct illumination | 3.1 | 40 |
| A | Forestadent C701-9330 | 1 min. transillumination from occlusal surface | 2.2 | 40 |
| A | Forestadent C701-9330 | 2 mins. transillumination from occlusal surface | 6.1 | 40 |
| A | Forestadent C701-9330 | 1 min. transillumination from occlusal surface | 3.1 | 80 |
| A | Forestadent mini-mono 701-3230 | 2 mins. transillumination from occlusal surface | 4.1 | 80 |
| B | Forestadent C701-9330 | 1 min transillumination from occlusal surface | 2.2 | 40 |
| B | Forestadent C701-9330 | 2 mins transillumination from occlusal surface | 4.0 | 40 |
| B | Oradent perforated 232 C 522 | 1 min direct illumination | 5.2 | 80 |
| B | Oradent perforated 232 C 522 | 30 secs direct illumination | 2.3 | 80 |
| B | Forestadent Mini-mono 701-3230 | 2 mins transillumination from occlusal surface | 4.5 | 80 |

In a clinical situation, the maximum force exerted by fixed appliances is equivalent to approximately 2.5k supported load, but the force is often much less. The above compositions may therefore be used as orthodontic adhesives and require only short cure from harmless radiation of visible light. The use of visible light cured compositions enables cure to be effected by radiation through a tooth, so ensuring homogeneous cure over the surface of a bracket, in particular a foil bracket. Ultra violet light cannot effect such a cure because it is strongly absorbed by the tooth material.

What we claim is:

1. A composition comprising the following components (a–c) intimately mixed together (a) a particulate siliceous material having particles below 10 μm in their longest dimension,
(b) a liquid or liquifiable polymerizable organic medium,
(c) a dispersing agent containing a mixture of compounds comprising a phosphorus oxyacid having the formula

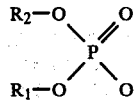

wherein $R_1$ is an organic group containing a terminal chain which is either a hydrocarbon group having at least six carbon atoms or a polyether of molecular weight greater than 200 (preferably from 500–10,000) $R_2$ is either a group as specified for $R_1$, a hydrogen atom, or a hydrocarbyl or substituted hydrocarbyl group not having a terminal chain of at least six carbon atoms and an organic basic nitrogen compound having the formula

wherein $Z_1$ is a group as specified for $R_1$ before and $Z_2$ and $Z_3$ which may be the same or different, are as specified for $R_2$ before.

2. A composition as claimed in claim 1 wherein the siliceous material is silica.

3. A composition as claimed in claim 2 wherein the silica is a colloidal form.

4. A composition as claimed in claim 1 wherein the medium is an acrylate or methacrylate monomer.

5. A composition as claimed in claim 1 wherein the liquid or liquifiable organic medium contains functional groups reactive with condensation catalysts or promoters.

6. A composition as claimed in claim 5 wherein the functional group is a hydroxyl group.

7. A composition as claimed in claim 1 wherein the medium is a vinyl urethane.

8. A composition as claimed in claim 1 wherein the group $R_1$ in the dispersing agent mixture comprises a longchain alkyl group containing from 8 to 22 carbon atoms.

9. A composition as claimed in claim 1 wherein the group $R_1$ in the dispersing agent mixture contains a polyoxyethylene or polyoxypropylene chain.

10. A composition as claimed in claim 1 wherein the group $R_2$ in the dispersing agent mixture is a group identical to $R_1$ or is a hydrogen atom.

11. A composition as claimed in claim 8 wherein the group $Z_1$ is a long chain alkyl group containing from 8 to 22 carbon atoms.

12. A composition as claimed in claim 8 wherein the groups $Z_2$ and/or $Z_3$ are hydrogen, a lower alkyl group containing less than six carbon atoms, a phenyl or a benzyl group.

13. A composition as claimed in claim 1 wherein the molar proportions of acid to base in the dispersing agent mixture is from 0.5:1 to 100:1.

14. A composition as claimed in claim 13 wherein the proportion is from 1:1 to 3:1.

15. A composition as claimed in claim 1 wherein a silane reactive to the siliceous solid is present in the composition.

16. A composition as claimed in claim 15 wherein the silane is a silane containing polymerisable groups.

17. A dispersion of a siliceous solid in an organic medium made from a composition as claimed in claim 1.

18. A dispersion as claimed in either claim 15 or claim 16 wherein the dispersion contains from 5 to 90% by weight of the siliceous solid.

19. A dispersion as claimed in claim 20 wherein the silica has an average particle size below 1 μm.

20. A dental composition which is a fluid composition comprising:
(a) a particulate siliceous material having particles below 1 μm in their longest dimension;
(b) a liquid or liquifiable organic medium which is either a vinyl urethane or the reaction product of a bisphenol with a glycidyl alkacrylate
(c) a dispersing agent containing a mixture of compounds comprising a phosphorus oxyacid having the formula:

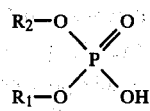

where $R_1$ is an organic group containing a terminal chain which is either a hydrocarbon group having at least six carbon atoms or a polyether of molecular weight greater than 200, preferably from 500–10,000, $R_2$ is either a group as specified for $R_1$, a hydrogen atom, or a hydrocarbyl or substituted hydrocarbyl group not having a terminal chain of at least six carbon atoms and an organic basic nitrogen compound having the formula:

wherein $Z_1$ is a group as specified for $R_1$ before and $Z_2$ and $Z_3$, which may be the same or different, are as specified for $R_2$ and
(d) a free radical generative catalyst for polymerisation of the organic medium.

21. A dental composition as claimed in claim 20 in which the vinyl urethane is a polymerisable prepolymer containing at least two polymerisable ethylenically unsaturated groups and being the reaction product of a urethane prepolymer and an ethylenically unsaturated monomer reactive with the urethane prepolymer.

22. A dental composition as claimed in claim 21 wherein the organic medium also contains 50 to 150% by weight of the vinyl urethane of at least one ethylenically unsaturated monomer.

23. A dental composition as claimed in claim 22 in which the free radical generative catalyst is activatable with radiation having a wavelength in the range 230 mμ to 500 mμ.

24. A dental composition as claimed in claim 23 in which the free radical generative catalyst is activatable with radiation having a wavelength in the range 400 mμ to 500 mμ.

25. A dental composition as claimed in claim 24 in which the free radical generative system comprises at least one photosensitiser selected from fluorenone, substituted derivatives thereof, and α-diketones having the structure

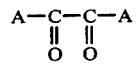

in which the groups A, which may be the same or different, are hydrocarbyl groups or substituted hydrocarbyl groups and at least one reducing agent capable of reducing the photosensitiser when the photosensitiser is in an excited state.

26. A small container containing a composition as claimed in claim 23.

27. A composition comprising the following components (a–c) intimately mixed together
    (a) a particulate siliceous material having particles below 10 μm in their longest dimension,
    (b) a liquid or liquifiable polymerizable organic medium not containing acidic or basic groups,
    (c) a dispersing agent containing a mixture of compounds comprising a phosphorus oxyacid having the formula

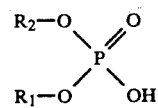

wherein $R_1$ is an organic group containing a terminal chain which is either a hydrocarbon group having at least six carbon atoms or a polyether of molecular weight greater than 200 (preferably from 500–10,000) $R_2$ is either a group as specified for $R_1$, a hydrogen atom, or a hydrocarbyl or substituted hydrocarbyl group not having a terminal chain of at least six carbon atoms and an organic basic nitrogen compound having the formula

wherein $Z_1$ is a group as specified for $R_1$ before and $Z_2$ and $Z_3$ which may be the same or different, are as specified for $R_2$ before.

* * * * *